(12) United States Patent
Kulikowski

(10) Patent No.: US 8,313,781 B2
(45) Date of Patent: Nov. 20, 2012

(54) LOW TOXICITY COMPOSITION FOR PROMOTING PLANT GROWTH

(76) Inventor: Henry S. Kulikowski, Cape Coral, FL (US)

( * ) Notice: Subject to any disclaimer, the term of this patent is extended or adjusted under 35 U.S.C. 154(b) by 0 days.

(21) Appl. No.: 12/744,232

(22) PCT Filed: Sep. 30, 2009

(86) PCT No.: PCT/US2009/059024
§ 371 (c)(1),
(2), (4) Date: Jul. 8, 2010

(87) PCT Pub. No.: WO2010/039829
PCT Pub. Date: Apr. 8, 2010

(65) Prior Publication Data
US 2011/0003014 A1 Jan. 6, 2011

Related U.S. Application Data

(60) Provisional application No. 61/101,241, filed on Sep. 30, 2008.

(51) Int. Cl.
| | |
|---|---|
| *A01N 59/02* | (2006.01) |
| *A61K 33/04* | (2006.01) |
| *A01N 59/00* | (2006.01) |
| *A01N 37/00* | (2006.01) |
| *A01N 65/00* | (2009.01) |
| *A01N 59/24* | (2006.01) |
| *A01N 36/752* | (2006.01) |
| *A61K 36/00* | (2006.01) |
| *A61K 36/54* | (2006.01) |
| *A61K 36/61* | (2006.01) |
| *A61K 36/53* | (2006.01) |
| *A61K 36/899* | (2006.01) |

(52) U.S. Cl. ........ 424/705; 424/725; 424/736; 424/739; 424/742; 424/745; 424/750; 504/119; 504/123; 504/188; 504/313

(58) Field of Classification Search ................ 424/705, 424/725, 736, 739, 742, 745, 750
See application file for complete search history.

(56) References Cited

U.S. PATENT DOCUMENTS

| | | | | |
|---|---|---|---|---|
| 6,103,768 | A * | 8/2000 | Savage et al. ................ | 514/627 |
| 6,548,085 | B1 * | 4/2003 | Zobitne et al. ............... | 424/725 |
| 2005/0129662 | A1 * | 6/2005 | Lameri ......................... | 424/93.4 |
| 2007/0287632 | A1 * | 12/2007 | Pohoreski ..................... | 504/189 |

FOREIGN PATENT DOCUMENTS
EP 1915906 A1 * 4/2008

OTHER PUBLICATIONS

Di Menna et al., 1981, J. of the Science of Food and Agriculture, 32(12): 1151-1156.*
http://chemicalland21.com/industrialchem/inorganic/sodium%020hypochlorite.htm (2005).*
http://en.wikipedia.org/wiki/Sodium-_percarbonate (1997-2005).*
Chemical Land 21 Datasheet [online], 2000 [retrieved Mar. 28, 2012]. Retrieved from the Internet: URL <chemicalland21.com/industrialchem/inorganic/sodium%20hypochlorite.htm>.*
"Sodium percarbonate" [online], 1999 [retrieved Mar. 28, 2012]. Retrieved from the Internet: URL <en.wikipedia.org/wiki/Sodium_percarbonate>.*
DiMenna et al., "The Effects of Some Additives on the Microflora of Silage," 1981, J. Sci. Food Agric., 32(12): 1151-1156.*
"Sodium Hypochlorite", Chemical Land 21 Datasheet [online], 2000 [retrieved Jul. 11, 2012] Retrieved from the Internet: <URL: http://chemicalland21.com/industrialchem/inorganic/sodium%20hypochlorite.htm>.*
"Sodium percarbonate", Wikipedia [online], 1999 [retrieved Jul. 11, 2012] Retrieved from the Internet: URL<http://en.wikipedia.org/wiki/Sodium_percarbonate>.*
Abstract of EP1915906A1 to Peltier et al., Apr. 2008.*

* cited by examiner

*Primary Examiner* — Richard Schnizer
*Assistant Examiner* — Jane C Oswecki
(74) *Attorney, Agent, or Firm* — Patent Procurement Services

(57) ABSTRACT

A composition for promoting plant growth includes sulfur, soybean oil, and an emulsifier of a fatty acid and a saponifying aqueous base together forming an emulsion, or a soap or a detergent acting as an emulsifier. Regardless of the form of the emulsifier, a composition as applied to vegetation which has a basic pH of between 7.5 and 11 appears to improve efficacy. Specific aqueous compositions as applied for promoting plant growth include 0.05 to 2 total weight percent sulfur, 0.05 to 2 total weight percent soybean oil, 0.05 to 2 total weight percent fatty acid and an aqueous base present to provide a basic pH of between 7.5 and 11. A concentrate for the composition which upon dilution with water is well suited for spraying and promotion of plant growth is provided. Another specific composition for promoting plant growth consists of 0.05 to 2 total weight percent sulfur, 0.05 to 2 total weight percent soybean oil, an aqueous base present to yield an as applied pH of 7.5 to 11, and optionally at least one of a biostatic, an oxidizer, a soap, a detergent, a natural oil, or combination thereof.

20 Claims, 1 Drawing Sheet

LOW TOXICITY COMPOSITION FOR PROMOTING PLANT GROWTH

CROSS-REFERENCE TO RELATED APPLICATIONS

This application is the U.S. national phase of PCT/US2009/059024 filed Sep. 30, 2009, which claims priority of U.S. Provisional Patent Application Ser. No. 61/101,241 filed Sep. 30, 2008, which is incorporated herein by reference.

FIELD OF THE INVENTION

The present invention in general relates to a low toxicity composition operative as a fungicide and insecticide for the treatment of agricultural and horticultural plantings and in particular to a composition lacking a synthetic halogenated or heterocyclic active compound.

BACKGROUND OF THE INVENTION

The treatment of insect infestation and fungus growth in crop plants and horticulture represents a considerable cost and creates a series of undesired consequences. Insecticide and fungicide compounds currently in use have a degree of toxicity as well as producing residues that accumulate in soil and runoff therefrom. These residues also impact localized ecology and often are injurious to beneficial insects and/or soil dwelling organisms. Representative of the active insecticide and fungicide compounds that have been employed are halogenated synthetic compounds, heterocyclic synthetic organic compounds, and inorganic copper compounds.

An older active compound that is again finding favor because of the aforementioned problems associated with synthetic organic materials and inorganic copper compounds is elemental sulfur. Elemental sulfur while having antifungal properties has limited activity against insects while having unattractive delivery properties as a powder or slurry that make it difficult to adhere to nonhorizontal vegetation surfaces. To overcome such problems vegetable oil has been added to spray formulations and through mechanical mixing forms an emulsion with adhesion advantages to plant surfaces while also imparting a lipophilic character to the composition that is able to wet the waxy cuticle associated with a leaf surface. U.S. Patent Application Publication 2005/0129662 is exemplary thereof.

Unfortunately, such vegetable oil emulsions that contain an active agent tend to phase segregate and have limited properties to penetrate waxy surface coatings associated with a variety of funguses and insect cuticles.

Thus, there exists a need for a composition of low toxicity that is amenable to effectively treat fungal and insect infestations of plants.

SUMMARY OF THE INVENTION

A composition for promoting plant growth includes sulfur, soybean oil, and an emulsifier of a fatty acid and a saponifying aqueous base together forming an emulsion, or a soap or a detergent acting as an emulsifier. Regardless of the form of the emulsifier, a composition as applied to vegetation which has a basic pH of between 7.5 and 11 appears to improve efficacy. Specific aqueous compositions as applied for promoting plant growth include 0.05 to 2 total weight percent sulfur, 0.05 to 2 total weight percent soybean oil, 0.05 to 2 total weight percent fatty acid and an aqueous base present to provide a basic pH of between 7.5 and 11. A concentrate for the composition which upon dilution with water is well suited for spraying and promotion of plant growth is provided. Another specific composition for promoting plant growth consists of 0.05 to 2 total weight percent sulfur, 0.05 to 2 total weight percent soybean oil, an aqueous base present to yield an as applied pH of 7.5 to 11, and optionally at least one of a biostatic, an oxidizer, a soap, a detergent, a natural oil, or combination thereof.

DETAILED DESCRIPTION OF THE PREFERRED EMBODIMENTS

Figure 1:
FIG. 1 is a photograph of an orange tree prior to application of an inventive composition.
Figure 2:
FIG. 2 is a photograph of the same tree 120 days later showing clearance of signs of infestation by aphids, psyllid bugs, and tristeza.

A composition is provided for promoting plant growth by operating as an antifungal and insecticide. The composition contains sulfur, a soybean oil, a fatty acid and an aqueous base that upon mixing with the aforementioned components forms an emulsion. The fatty acid and base are appreciated to saponify and be replaced with a pH adjusted soap or detergent. A natural oil distinct from soybean oil is also optionally added. A biostatic is provided to promote storage stability of a composition or concentrate thereof and maintain the pH of the composition between 7.5 and 11 and preferably between 8 and 9. The resulting composition upon dilution with water is well suited for spray application to foliage as a treatment, or a prophylactic for fungal and insect infestations. As the inventive composition does not require synthetic heterocyclic compounds or synthetic halogenated organic compounds as active agents to treat fungal or insect infestations, the inventive composition eliminates many of the negative environmental impacts associated with crop spraying including water and soil contamination, runoff, and incidental lethality to beneficial soil microbes or insects.

An inventive composition has proven highly effective for spring application to citrus trees for prevention and cure of a variety of infestations including citrus canker, citrus greening, tristeza, molds, rust, mildew, moss, leaf spots, aphids, thirps, and mites. Soybean plants suffering fungal infection have also responded favorably to application of an inventive composition and are exemplary of the crops so treated.

An inventive composition is preferably provided as a concentrate to facilitate transport and storage with a quantity of water diluent being added prior to spray application. An inventive composition concentrate includes sulfur, soybean oil, a fatty acid, and an aqueous base that together form an emulsion. A composition concentrate has a composition as detailed in Table 1:

TABLE 1

Inventive composition concentrate as a water based emulsion

| Component | Typical Total Wt. Percent | Preferred Total Wt. Percent |
|---|---|---|
| Sulfur | 1-10 | 1-5 |
| Soybean oil | 0.2-8 | 0.5-4 |
| Fatty acid or surfactant/soap | 1-20/0.1-5 | 1-10/0.2-3 |
| Biostatic | 0-10 | 1-5 |
| Natural oils | 0-20 | 1-10 |
| Oxidizer | 0-5 | 0.5-3 |
| Aqueous base | to pH 7.5-12 | to pH 7.5-10 |

An inventive composition concentrate while itself amenable to dispersion onto foliage as a fungicide or insecticide is preferably diluted with 2 to 5 parts per weight water per part by weight of composition concentrate. The resultant emulsion formed with the combination of water diluent and inventive composition concentrate has a pH adjusted to between 7.5 and 11. For citrus and soybean application in particular, the pH is preferably between 8 and 9.

The fatty acid component is selected to be compatible with the other composition components and illustratively includes $C_{10}$-$C_{24}$ acids such as oleic acid, octanoic acid, stearic acid, palmitic acid, linoleic acid, arachidonic acid and palmitoleic acid.

An aqueous base component of an inventive composition is selected to increase the pH of the composition and dissolve in water. Preferably, the aqueous base is dissolved in water and the aqueous base solution then mixed with the other composition components to form an emulsion. Base compositions operative herein illustratively include sodium hydroxide, potassium hydroxide, and ammonium hydroxide, calcium hydroxide, and lithium hydroxide. It is appreciated that a base can also provide plant fertilizer or soil amendment properties.

As an alternative to saponification of a fatty acid through reaction with a base to form an emulsifying soap, it is appreciated that a soap or a detergent is mixed in complete or partial substitution of the fatty acid. However, it has been found that the basic pH of between 7.5 and 11 as applied to a plant also benefits the treatment efficacy of the target plant. Without intending to be bound by a particular theory, waxy cuticles associated with plant leaves, insects and fungi are rendered partially porous at these pH values without causing damage as seen under more caustic pH values. As a result, the inclusion of a soap and an aqueous base to achieve an as-applied pH of 7.5 and 11 is of benefit although not essential.

Optionally, natural oil is added to an inventive composition concentrate. The natural oil improves the emulsion properties of the resulting composition. Natural oils operative herein illustratively include canola oil, corn oil, fish oil, cod liver oil, sunflower oil, peanut oil, linseed oil, cottonseed oil, and combinations thereof.

Optionally, a biostatic is provided to stabilize an inventive composition or concentrate thereof and also to operate as a bacteriostatic or fungistatic. Suitable biostatics illustratively include borates, boric acid, benzoate, tetracyclines, sulphonamides spectinomycin, trimethoprom, chloramphenicol, macrolides, lincosamides, lactoferrin and combinations thereof. Inventive compositions inclusive of a biostatic demonstrate superior fungal control and greening of foliage.

Optionally, an oxidizer is provided as a bacteriostatic or fungistatic. A suitable oxidizer is stable at basic pH and illustratively includes hypochlorites and percarbonates, such as the sodium salts thereof. Inventive compositions inclusive of an oxidizer demonstrate superior fungal control and greening of foliage.

Without intending to be bound by a particular theory, an inventive composition shows superior antifungal and insecticide properties relative to sulfur when soybean oil is present. Additionally, when sulfur and soybean oil are combined with base and fatty acid, still greater efficacy is observed and believed to be the result of the composition being able to saponify a waxy cuticle associated with insects, leaf surfaces and/or fungus, thereby achieving greater action of these active agents, as well as optional biostatics and/or oxidizers.

A process for treating foliage suffering from an infestation of fungus or insects or to prevent such an infestation includes the application of a composition to the foliage of the plant. The composition includes a diluted composition concentrate per Table 1 by a factor of between 3 and 40 and preferably between 5 and 30, and most preferably between 10 and 20. Dilution occurs in water, an aqueous polymer solution, an aqueous polymer dispersion, or aqueous emulsion. By way of example, prolonged treatment of bush, tree and orchard crop woody portions of trunk, branches and bark are facilitated by dilution of an inventive composition concentrate into an aqueous polymer solution, dispersion, or emulsion that dries to provide a coating retaining an inventive composition in contact with woody portions of a plant. An aqueous latex emulsion represents a preferred aqueous emulsion for the dilution of an inventive composition concentrate; such emulsions are commonly available as consumer latex bases for paints regardless of whether pigmented and typically include 30 to 70 weight percent solids of the latex emulsion. Aqueous polymers suitable for forming solutions and dispersion operative as a diluent for an inventive composition concentrate include polyethylene glycols, acrylates, poly vinyl pyrrolidones, and esterified castor oil derivatives, and silanol containing organo polyxiloxanes, guar gums, and cellulosic based polymer derivatives dispersible in water. Such polymers are typically present in the diluent at from 0.1 to 5 weight percent of diluent as determined prior to inventive composition concentrate dilutions.

An inventive composition when applied in the spring provides an inexpensive treatment composition with a long effective period and precludes environmental toxicity associated with conventional synthetic insecticide formulations. Application during other times of the annual growth cycle provides enhanced plant growth even in instances when the plant is suffering no visible infestations. The mechanism of this growth enhancement effect is unknown.

An inventive composition is also well suited for the treatment of cultivated vegetable crops such as tomato, potato, soybeans, leaf vegetables, corn, wheat, carrots, onion, celery, melons, strawberry, squash, and legumes; berry crops such as blueberry, raspberry, and currant; ornamentals such as roses, tulips, chrysanthemums, orchids, and petunias; fruit trees such as citrus, cherry, apple, pear, fig, almond, walnut, olive, peach, and plum; vines such as grape and kiwi; and ornamental trees such as gingko, dogwood, flowering pear, redbud, birch, and willow.

The present invention is further detailed with respect to the following example.

EXAMPLE 1

An aqueous fully diluted inventive composition is prepared containing by total weight percentage potassium benzoate 0.5%, canola oil 0.5%, oleic acid 0.5%, sulfur 0.2%, soybean oil 0.2%, potassium hydroxide 0.7% with the remainder being water so as to form an emulsion with a pH of 8.5. The resulting emulsion is spray applied after spring leafing to orange trees exhibiting simultaneous infestation by aphids, Asian citrus bugs, psyllid bugs, and tristeza fungal infestation. The emulsion was applied as a single spraying in an amount sufficient to wet the leaves and woody portions of the trees in an amount of approximately 4 liters per tree or about 100 gallons per acre. The appearance of a representative tree prior to application of an inventive emulsion composition as detailed in this example is provided in FIG. 1. FIG. 2 depicts the same tree 120 days after application of the inventive composition according to this example. FIG. 2 shows an appreciable improvement in foliage color and quantity with no observation of aphids.

EXAMPLE 2

An aqueous fully diluted inventive composition is prepared containing by total weight percent 0.5% canola oil, 0.5% oleic acid, 0.3% sulfur, 0.2% soybean oil, 0.5% potassium hydroxide, and 0.3% sodium hypochlorite, with the remainder being water. The resulting emulsion is applied to soybean plants suffering from rust infection. After spraying to wet foliage once weekly for 3 consecutive weeks, visible signs of rust are no longer noted.

EXAMPLE 3

The composition of Example 2 is reproduced with the exception that oleic acid is omitted and replaced with 0.1% sodium lauryl sulfate. The resulting composition achieves a comparable level of rust control on soybean plants.

EXAMPLE 4

The composition of Example 2 is reproduced with the exception that sodium hypochlorite is replaced with a like amount of sodium borate. The resulting composition is effective in fungus and psyllid bug control on citrus trees in Florida and is accepted to also control fungus and insects in soybeans pending field data.

EXAMPLE 5

The composition of Example 2 is reproduced with the exception that instead of water as the diluent, a tenfold concentrate is dispersed in a 60% by weight solids latex emulsion. Application of the resulting latex to citrus tree trunks 8 weeks prior to blossoming season reduced occurrence and severity of aphid and thrip infection relative to control trees planted with only the diluent latex composition. Tristeza also occurs in reduced frequency and severity.

EXAMPLE 6

An inventive composition of Example 1 or a concentrate thereof is applied to the skin of a subject suffering from psoriasis or an inflammatory fungal infection. The composition applied once a day onto the affected area and is noted to immediately reduce inflammation. After a period of 5 to 10 days the affected area is noted to have cleared.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition comprising:
- water;
- sulfur;
- soybean oil;
- an emulsifier of a fatty acid in the presence of an aqueous base that together form an emulsion, or a soap or a detergent; and
- wherein said composition has a basic pH of between 8 and 9.8.

2. The composition of claim 1 wherein said emulsifier is said fatty acid and said aqueous base.

3. The composition of claim 1 wherein said emulsifier is said soap or said detergent.

4. The composition of claim 1 further comprising a natural oil.

5. The composition of claim 4 wherein said natural oil includes at least one of canola oil, fish oil, corn oil, cottonseed oil, and peanut oil.

6. The composition of claim 1 further comprising a biostatic.

7. The composition of claim 6 wherein said biostatic is benzoate.

8. The composition of claim 4 wherein said natural oil comprises at least canola and fish oils.

9. The composition of claim 1 further comprising an oxidizer of a hypochlorite or percarbonate salt.

10. A concentrate for the composition of claim 1 comprising:
- sulfur present from 1 to 10 total weight percent of the concentrate;
- soybean oil present from 1 to 10 total weight percent of the concentrate;
- a fatty acid present from 1 to 10 total weight percent of the concentrate;
- an aqueous base present from 3 to 20 total weight percent of the concentrate; and
- water present to form a storage stable and homogenous emulsion.

11. A concentrate for a composition consisting of:
- sulfur present from 1 to 5 total weight percent of the concentrate;
- soybean oil present from 1 to 5 total weight percent of the concentrate;
- a fatty acid present from 3 to 10 total weight percent of the concentrate;
- an aqueous base present from 5 to 15 total weight percent of the concentrate;
- optionally a polymer capable of drying to a coating, a biostatic, a soap, a detergent, a natural oil, an oxidizer of a hypochlorite or percarbonate salt, or a combination thereof;
- water present to form a storage stable and homogenous emulsion;
- wherein said homogenous emulsion acts as an emulsifier of a fatty acid in the presence of an aqueous base that together form an emulsion, or a soap or a detergent; and
- wherein said composition has a basic pH of between 8 and 9.8.

12. The concentrate of claim 11 wherein the biostatic is present from 3 to 10 total weight percent of the concentrate and is benzoate.

13. The concentrate of claim 11 wherein said natural oil is present from 3 to 10 total weight percent of the concentrate.

14. A process for promoting plant growth comprising:
- diluting the concentrate of claim 10 in a solvent to form a composition for promoting plant growth; and
- applying said composition to a plant.

15. The process of claim 14 wherein the applying is by spraying or brushing on the plant.

16. The process of claim 14 wherein said solvent contains a polymer capable of forming a coating upon evaporation of the water of the concentrate and said solvent.

17. The process of claim 14 wherein said solvent and said polymer are present as a latex.

18. The process of claim 14 wherein the plant is vulnerable to or suffering infestation by a fungus or an insect.

19. The process claim 14 wherein the plant is one of tomato, potato, soybeans, leaf vegetables, corn, wheat, carrots, onion, celery, melons, strawberry, squash, legumes, blueberry, raspberry, currant, roses, tulips, chrysanthemums, orchids, petunias, citrus, cherry, apple, pear, fig, almond, walnut, olive, peach, plum, grape, kiwi, gingko, dogwood, flowering pear, redbud, birch, or willow.

20. The composition of claim 1 wherein said composition has a basic pH of between 8 and 9.

* * * * *